(12) United States Patent
Adachi et al.

(10) Patent No.: US 9,557,264 B2
(45) Date of Patent: Jan. 31, 2017

(54) AUTOMATIC ANALYSIS DEVICE, AND AUTOMATIC ANALYSIS METHOD

(71) Applicant: HITACHI HIGH-TECHNOLOGIES CORPORATION, Tokyo (JP)

(72) Inventors: Sakuichiro Adachi, Tokyo (JP); Hajime Yamazaki, Tokyo (JP); Masahiko Iijima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/414,782

(22) PCT Filed: Jun. 14, 2013

(86) PCT No.: PCT/JP2013/066483
§ 371 (c)(1),
(2) Date: Jan. 14, 2015

(87) PCT Pub. No.: WO2014/013823
PCT Pub. Date: Jan. 23, 2014

(65) Prior Publication Data
US 2015/0219556 A1    Aug. 6, 2015

(30) Foreign Application Priority Data

Jul. 20, 2012    (JP) .................................. 2012-161846

(51) Int. Cl.
*G01N 21/00* (2006.01)
*G01N 21/64* (2006.01)
(Continued)

(52) U.S. Cl.
CPC .......... *G01N 21/49* (2013.01); *G01N 15/1434* (2013.01); *G01N 21/253* (2013.01);
(Continued)

(58) Field of Classification Search
CPC ........ G01N 21/00; G01N 21/64; G01N 21/66; G01N 15/06; G01N 35/00; G01N 21/75; G01N 21/62
(Continued)

(56) References Cited

U.S. PATENT DOCUMENTS 4,234,539 A * 11/1980 Ginsberg et al. ............... 422/64
4,267,149 A * 5/1981 Bruckner et al. ............... 422/65
(Continued)

FOREIGN PATENT DOCUMENTS

EP    2 293 081 A2    3/2011
EP    2 541 233 A1    1/2013
(Continued)

OTHER PUBLICATIONS

C.F. Bohren, D.R. Huffman, Absorption and Scattering of Light by Small Particles, J. Wiley & Sons, 1983, pp. 82-129.
(Continued)

*Primary Examiner* — Brian J Sines
(74) *Attorney, Agent, or Firm* — Mattingly & Malur, PC

(57) ABSTRACT

To enable determination of if there is an influence of foreign-body reactions on the result of quantitative determination conducted with a scattered light measurement method. Proposed is an automatic analysis device including a light source configured to irradiate a reaction solution with light, a plurality of light receivers configured to receive scattered light generated from the reaction solution at different light-receiving angles, a first data processing unit configured to process reaction process data measured by one of the light receivers to quantitatively determine a concentration of a substance in the reaction solution, and a second data processing unit configured to determine if the quantitative determination of the concentration of the substance has been performed normally on the basis of a ratio of a
(Continued)

plurality of computed values, the plurality of computed values having been calculated from a plurality of pieces of reaction process data measured by the respective light receivers.

5 Claims, 8 Drawing Sheets

(51) Int. Cl.
| | |
|---|---|
| *G01N 21/66* | (2006.01) |
| *G01N 15/06* | (2006.01) |
| *G01N 21/49* | (2006.01) |
| *G01N 21/51* | (2006.01) |
| *G01N 15/14* | (2006.01) |
| *G01N 21/25* | (2006.01) |
| *G01N 21/27* | (2006.01) |
| *G01N 21/82* | (2006.01) |
| *G01N 35/02* | (2006.01) |
| *G01N 21/31* | (2006.01) |
| *G01N 21/47* | (2006.01) |
| *G01N 35/00* | (2006.01) |

(52) U.S. Cl.
CPC ........... *G01N 21/272* (2013.01); *G01N 21/51* (2013.01); *G01N 21/82* (2013.01); *G01N 35/025* (2013.01); *G01N 21/31* (2013.01); *G01N 2021/4711* (2013.01); *G01N 2021/825* (2013.01); *G01N 2035/00396* (2013.01); *G01N 2201/02* (2013.01); *G01N 2201/062* (2013.01); *Y10T 436/11* (2015.01)

(58) Field of Classification Search
USPC ....... 422/50, 68.1, 400, 82.05, 82.08, 82.09; 436/43, 164, 171, 172
See application file for complete search history.

(56) References Cited

U.S. PATENT DOCUMENTS

| | | | |
|---|---|---|---|
| 4,338,279 A * | 7/1982 | Orimo et al. | .................. 422/64 |
| 4,401,387 A | 8/1983 | Tokinage et al. | |
| 4,451,433 A | 5/1984 | Yamashita et al. | |
| 4,647,432 A * | 3/1987 | Wakatake | ....................... 422/64 |
| 4,796,197 A * | 1/1989 | Lissot et al. | .................... 702/19 |
| 6,469,311 B1 * | 10/2002 | Modlin et al. | ................. 250/576 |
| 6,791,676 B1 | 9/2004 | Meller | |
| 2011/0293476 A1 | 12/2011 | Adachi et al. | |

FOREIGN PATENT DOCUMENTS

| | | |
|---|---|---|
| JP | 04-250342 | 9/1992 |
| JP | 2001-141654 | 5/2001 |
| JP | 2011-174842 | 9/2011 |
| WO | 2011/105464 A1 | 9/2011 |

OTHER PUBLICATIONS

Extended European Search Report received in corresponding European Application No. 13820458.1 dated Jun. 10, 2016.

* cited by examiner

AUTOMATIC ANALYSIS DEVICE, AND AUTOMATIC ANALYSIS METHOD

TECHNICAL FIELD

The present invention relates to an automatic analysis device and an automatic analysis method for measuring the concentration of a substance in a sample.

BACKGROUND ART

An automatic analysis device, which irradiates a reaction solution obtained by reaction of a sample with a reagent with light, and calculates absorbance from the amount of transmitted light that has passed through the reaction solution in accordance with the Lambert-Beer's law, and then quantitatively determines the concentration of a substance in the sample from the amount of change of absorbance that occurred in a given period of time, is widely used (e.g., see Patent Literature 1). In such a device, a number of cells each holding a reaction solution are circumferentially arranged on a reaction disc. An absorbance measuring unit is arranged around the reaction disc that is rotationally driven, so that time-series data on the amount of light that has passed through the reaction solution (the amount of transmitted light) is acquired for about 10 minutes at intervals of once every 15 seconds. The time-series data herein is referred to as reaction process data. Absorbance is calculated from the amount of transmitted light, and the concentration of a substance is quantitatively determined from the amount of change of absorbance that occurred in a given period of time.

Reactions that are measured by an automatic analysis device include two types: a color reaction that uses a substrate and an enzyme, and immune agglutination that uses an antigen and an antibody. A method for quantitatively determining the concentration through a color reaction is referred to as a biochemical analysis. Examples of test items of the biochemical analysis include LDH (lactate dehydrogenase), ALP (alkaline phosphatase), and AST (aspartate-oxoglutarate aminotransferase). A method for quantitatively determining the concentration of a substance through immune agglutination is referred to as an immune assay. Examples of test items of the immune assay include CRP (C-reactive protein), IgG (immunoglobulin), and RF (rheumatoid factor). The concentration of a substance, which is measured through immune agglutination, in the blood is relatively low. Therefore, a reagent used is required to be highly sensitive. Thus, latex particles, which are obtained by sensitizing antibodies as a sensitizer on the surface of a reagent, are often used as a reagent. The latex particles with sensitized antibodies on the surface will aggregate via a substance to be measured, thereby forming an aggregate. The aggregate will grow with time. The higher the concentration of the substance, the larger the aggregate that is obtained after a given period of time has elapsed. According to the measurement methods so far, a reaction solution in which an agglutination reaction has progressed is irradiated with light, and the amount of transmitted light that has passed through the reaction solution is measured to quantitatively determine the concentration of the substance to be measured.

However, in recent years, a further increase in sensitivity is desired for the latex immunoassay, and attempts have been made to measure not transmitted light but scattered light. For example, a system (Patent Literature 2) is disclosed that measures absorbance and scattered light at the same time by separating the transmitted light from the scattered light using a diaphragm, for example.

CITATION LIST

Patent Literature

Patent Literature 1: U.S. Pat. No. 4,451,433 A
Patent Literature 2: JP 2001-141654 A

Non Patent Literature

Non Patent Literature 1: C. F. Bohren, D. R. Huffman, Absorption and Scattering of Light by Small Particles, J. Wiley &Sons, 1983

SUMMARY OF INVENTION

Technical Problem

A method for measuring scattered light is able to measure a reaction as a larger change than with a method for measuring transmitted light. Meanwhile, the method for measuring scattered light has a problem in that it is susceptible to influence of foreign-body reactions. Examples of foreign-body reactions include growth of air bubbles on the optical path due to deposition of dissolved oxygen, a nonspecific agglutination reaction of foreign matter in the blood, and a nonspecific agglutination reaction of dust in a reaction solution.

When such reactants are present on the measurement optical path, the amount of scattered light (i.e., the intensity of scattered light) exhibits a similar change to that when an agglutination reaction of latex particles occurs. Therefore, depending on the reaction process data, it has been impossible to clearly distinguish if the scattered light is the one obtained from a normal aggregate or the one obtained from foreign matter. Consequently, an increase of noise due to the influence of foreign matter, such as dust or air bubbles, has been problematic.

Solution to Problem

In order to solve the above problems, an automatic analysis device in accordance with the present invention includes a light source configured to irradiate a reaction solution with light, a plurality of light receivers configured to receive scattered light generated from the reaction solution at different light-receiving angles, a first data processing unit configured to process reaction process data measured by one of the light receivers to quantitatively determine a concentration of a substance in the reaction solution, and a second data processing unit configured to determine if the quantitative determination of the concentration of the substance has been performed normally on the basis of a ratio of a plurality of computed values, the plurality of computed values having been calculated from a plurality of pieces of reaction process data measured by the respective light receivers.

Advantageous Effects of Invention

According to the present invention, it is possible to determine if there is a large influence of foreign-body reactions on the result of quantitative determination of the concentration of a substance that is conducted with a scattered light measurement method. Other problems, configurations, and advantageous effects will become apparent from the following description of embodiments.

DESCRIPTION OF EMBODIMENTS

Hereinafter, embodiments of the present invention will be described with reference to the drawings. It should be noted that the embodiments of the present invention are not limited to those described below, and a variety of variations are possible within the spirit and scope of the invention.

[Embodiment 1]

This embodiment will describe the basic configuration of an automatic analysis device that has a function of determining the presence or absence of a foreign-body reaction that may influence measurement results, that is, a function of determining if the measurement results are normal, and a summary of the principle of the determination.

Figure 1:
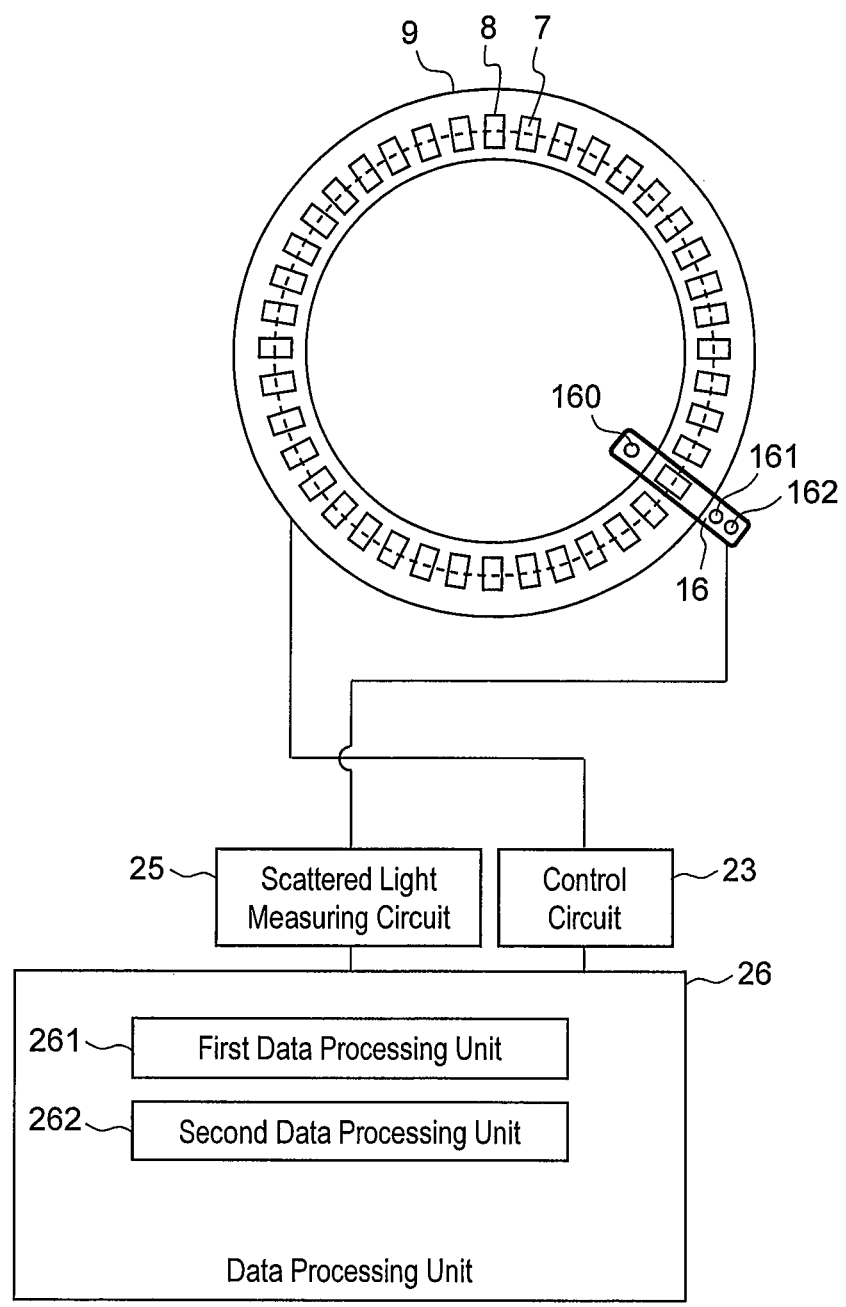
FIG. 1 illustrates the main configuration of an automatic analysis device (Embodiment 1).

FIG. 1 shows the schematic configuration of an automatic analysis device that measures scattered light from a reaction solution to quantitatively determine the concentration of a substance on the basis of a temporal change of the scattered light. It should be noted that the configuration of the automatic analysis device shown in FIG. 1 is used only to describe the basic concept of the invention as proposed in this specification.

The automatic analysis device includes a reaction disc 9 that holds cells 8, each of which stores a reaction solution 7 obtained by mixing a sample with a reagent, on the circumference of the disc and repeats rotation and stop, a light source 160 that irradiates each cell 8 with light, two light receivers 161 and 162 that receive scattered light generated from the reaction solution 7 at different light-receiving angles, a scattered light measuring circuit 25 that acquires data on the amount of light output from the two light receivers 161 and 162 at regular intervals, and outputs the data as reaction process data, a first data processing unit 261 that processes the reaction process data of the reaction solution measured with the light receiver 161 to quantitatively determine the concentration of a substance in the reaction solution, and a second data processing unit 262 that determines if the result of quantitative determination of the concentration of the substance is normal on the basis of the ratio of the computed values of the two pieces of reaction process data measured with the respective light receivers 161 and 162.

It should be noted that the automatic analysis device includes a control circuit 23 that controls rotation of the reaction disc 9 as well as light emission and light reception of the scattered light measuring unit 16 (i.e., the light source 160 and the light receivers 161 and 162). In addition, the automatic analysis device includes a data processing unit 26 that incorporates the first data processing unit 261 and the second data processing unit 262. It should be noted that each of the control circuit 23 and the data processing unit 26 may be either constructed as a control module or a computer that executes processing programs.

The automatic analysis device described in this embodiment is characterized by including the two light receivers 161 and 162 that receive scattered light at different angles from the irradiation direction (i.e., optical axis) of light that irradiates the reaction solution 7, and having a function of determining if the result of quantitative determination of the concentration of a substance is normal on the basis of the ratio of the computed values of the two pieces of reaction process data measured with the respective light receives 161 and 162. Using such a function, the automatic analysis device in accordance with this embodiment is able to, even when there is an influence of foreign-body reactions, inform an operator that the result of quantitative determination is influenced by the foreign-body reaction.

It should be noted that for the computed values of the two pieces of reaction process data, it is desirable to use computed values before calibration. In such a case, the value of quantitative determination can be checked without the influence of significant digits and the like.

Hereinafter, the reasons for providing the light receivers 161 and 162 that receive scattered light at different light-receiving angles will be described. An aggregate of latex particles and foreign matter in a reaction solution differ in their materials and size. Latex particles in a reagent for an automatic analysis device are often made of polystyrene, and the particle size thereof is considered to be about 0.1 to 0.3 μm. It should be noted that for measurement of the particle size, a variety of methods, such as a dynamic light scattering method, a laser diffraction method, a centrifugal sedimentation method, an FFF method, or an electrical detection method, can be used. When the concentration of a substance to be measured is low, the size of aggregated latex particles will not change almost at all on average, and the particle size thereof can thus be regarded as about 0.1 to 0.3 μm.

The material of the foreign matter in the reaction solution is unknown, but it is gas if the reaction solution contains dissolved oxygen. In other cases, the foreign substance may be regarded as having a similar refractive index to polystyrene. The foreign matter is considered to have a size of about roughly several μm since about the same amount of light as that of latex particles is detected although the size of the foreign matter is smaller than that of the latex particles.

In the measurement conducted with the scattered light measurement method, a difference in size between aggregated latex particles and foreign matter in the reaction solution is particularly important.

Figure 2:
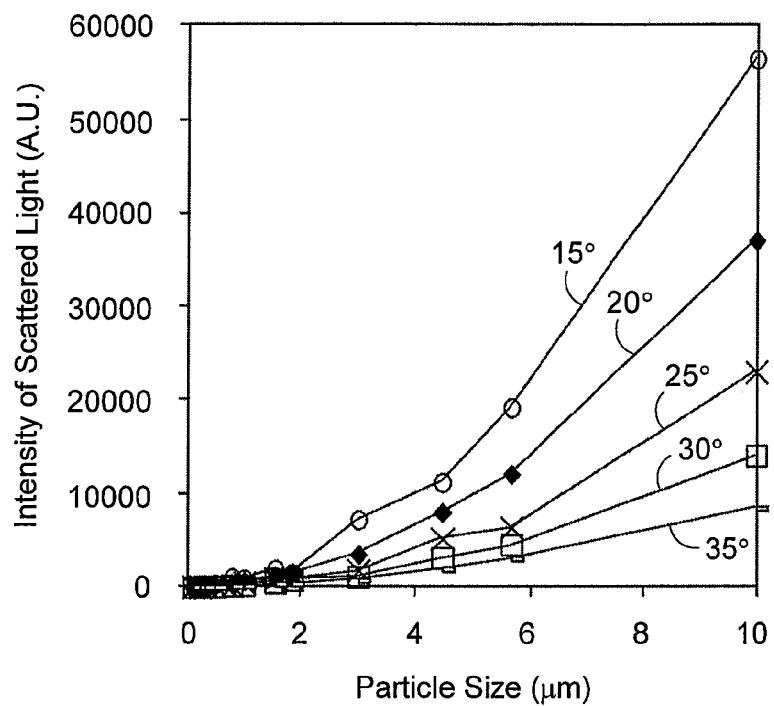
FIG. 2 shows the particle-size dependence of the intensity of scattered light from latex particles.

FIG. 2 shows the particle-size dependence of the amount of scattered light that is generated when a single particle of polystyrene (with a refractive index of 1.59) in water is irradiated with light with a wavelength of 700 nm, at each of light-receiving angles of 15°, 20°, 25°, 30°, and 35° in terms of angles in the air. The light-receiving angles are defined as angles with respect to the optical axis of the irradiation light. The Mie scattering theory was used to calculate such angles. The Mie scattering theory is described in Non Patent Literature 1, for example.

It is known that in the Mie scattering theory, scattered light has a property of generally gathering in the more front side (in the travelling direction of the irradiation light) as the size of a scattering particle is larger. Therefore, provided that the size of the scattering particle is unchanged, the amount of scattered light that is received tends to be larger as the light-receiving angle is smaller. The amount of scattered light from a reaction solution containing latex particles can be simply considered as the superposition of the amounts of scattered light from a single latex particle. Therefore, even when scattered light is received from a number of particles in a reaction solution, the amount of scattered light is estimated to be larger as the light-receiving angle is smaller.

Focusing on the dependence on the light-receiving angle, this embodiment will verify, when the light-receiving angle of the light receiver 161 is set to 20° and the light-receiving angle of the light receiver 162 is set to 30°, the relationship between the ratio of the amounts of scattered light that are received by the respective light receivers and the particle size.

Figure 3:
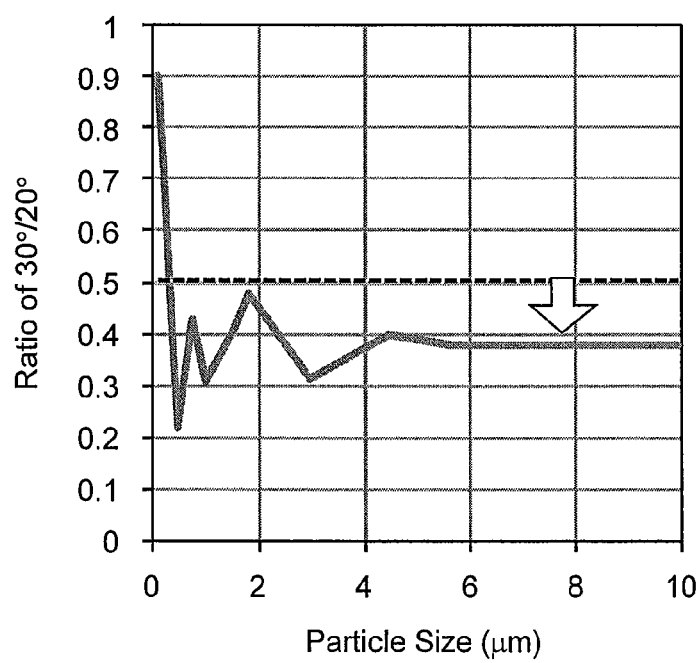
FIG. 3 shows the particle-size dependence of the intensity ratio of scattered light from latex particles (i.e., a ratio of 30°/20°).
Figure 4:
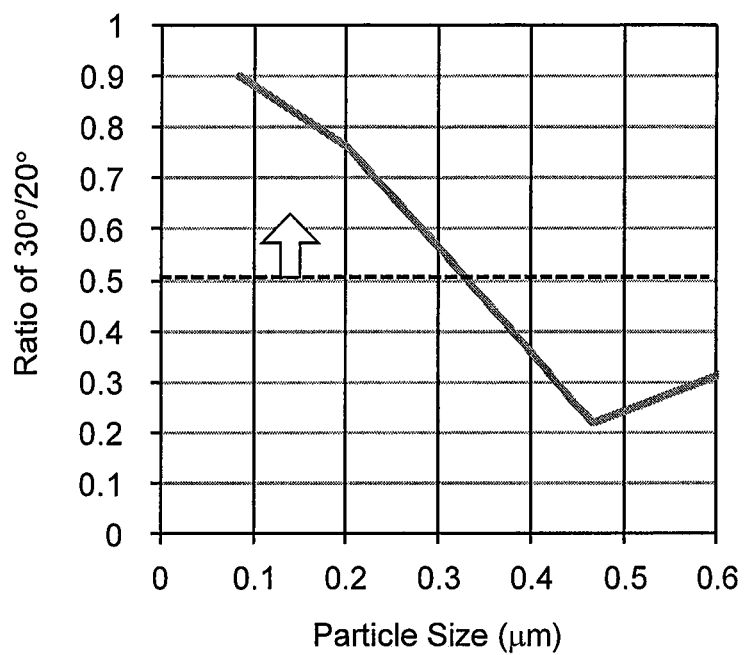
FIG. 4 shows the enlarged particle-size dependence shown in FIG. 2.

FIG. 3 shows the relationship between a value, which is obtained from dividing a computed value corresponding to the light receiver 162 with a light-receiving angle of 30° by a computed value corresponding to the light receiver 161 with a light-receiving angle of 20° (hereinafter referred to as a "ratio of 30°/20°"), and the particle size. FIG. 4 shows the relationship between the ratio of 30°/20° and the particle size when the particle size is less than or equal to 0.6 μm in FIG. 3.

As is clear from FIG. 3, in the range of the particle size of less than or equal to 10 μm, the ratio of 30°/20° generally tends to be smaller as the size of the scattering particles is larger. Regardless of whether the particles in the reaction solution are air bubbles, latex particles, or the like, similar properties are exhibited in this range. In addition, from FIG. 3, the ratio of 30°/20° when a foreign-body reaction (i.e., a reaction by particles that are considered to have a size of about several μm) occurs is generally estimated to be less than or equal to 0.5.

Meanwhile, as shown in FIG. 4, the ratio of 30°/20° for an aggregate of latex particles (the particle size of which can be regarded as about 0.1 to 0.3 μm) can be generally estimated to be about 0.9 to 0.5.

Herein, the two light receivers 161 and 162 desirably receive scattered light that have passed through the same transmissive plane of the cell 8. This is because, if the two light receivers 161 and 162 receive scattered light that have passed through different transmissive planes of the cell 8, the measurement results are influenced by variations of the transmissive planes. In order to satisfy the condition that the scattered light should pass through the same transmissive plane, the light-receiving angles of the two light receivers 161 and 162 are desirably selected from a range of about less than or equal to 35°. When such condition on the angle is satisfied, there is no possibility that the two light receivers 161 and 162 may receive scattered light that have passed through different planes of the cell 8. Consequently, the accuracy of determination of if the measurement results are defective can be improved. It should be noted that the two light-receiving angles in this embodiment are only exemplary. Thus, the present invention can also be applied to cases where three or more light-receiving angles are provided.

The first data processing unit 261 calculates the amount of change generated in a given period of time from the reaction process data acquired at a given light-receiving angle, as a computed value, and quantitatively determines the concentration of a substance to be measured on the basis of the computed value. In this embodiment, the reaction process data measured with the light receiver 161 is used as the target to be processed.

The second data processing unit 262 calculates computed values from the two pieces of reaction process data acquired at the respective light-receiving angles, and calculates the ratio of the two computed values as the computed value ratio. The computed value ratio herein shows the same tendency as the ratio of the amounts of scattered light.

The second data processing unit 262 in this embodiment compares the ratio of the computed value when the light-receiving angle is 30° to the computed value when the light-receiving angle is 20° (i.e., the ratio of 30°/20°) with a predetermined threshold (in this embodiment, two thresholds that are the maximum value and the minimum value), and determines if there is a large influence of scattered light from foreign matter. That is, the second data processing unit 262 determines if the measured amount of scattered light originates from scattered light from latex particles or scattered light from foreign matter.

Specifically, when the computed value ratio of 30°/20° is greater than 0.5, it is determined that the quantitatively determined concentration is not influenced by scattered light from foreign matter. Meanwhile, when the computed value ratio of 30°/20° is less than 0.5, it is determined that the quantitatively determined concentration is influenced by scattered light from foreign matter.

Herein, if it is determined that the influence of scattered light from foreign matter is large, the second data processing unit 262 or the control circuit 23 outputs an alarm to that effect via an output device (not shown). The output patterns of the alarm include a method using characters or images, a method using sound, and a method of lighting or blinking a warning lamp or the like.

With the automatic analysis device in accordance with this embodiment, it is possible to determine if the quantitatively determined concentration includes an influence of foreign-body reactions. Thus, the concentration of the substance to be measured can be quantitatively determined with high accuracy using a scattered light measurement method.

[Embodiment 2]
[Device Configuration]

Hereinafter, a specific example of an automatic analysis device that uses the measurement principle in Embodiment 1 will be described. This embodiment will describe an automatic analysis device that executes quantitative determination of the concentration and determination of if the result of quantitative determination is normal or abnormal on the basis of the measured amounts of scattered light that have been output in the directions of about 20° and 30° with respect to the irradiation direction of the cell 8.

It should be noted that the automatic analysis device in this embodiment has a function of displaying on a screen if the result of quantitative determination is correct on the basis of the ratio of computed values that are calculated from a plurality of pieces of reaction process data obtained by measuring scattered light corresponding to the respective light-receiving angles.

Figure 5:
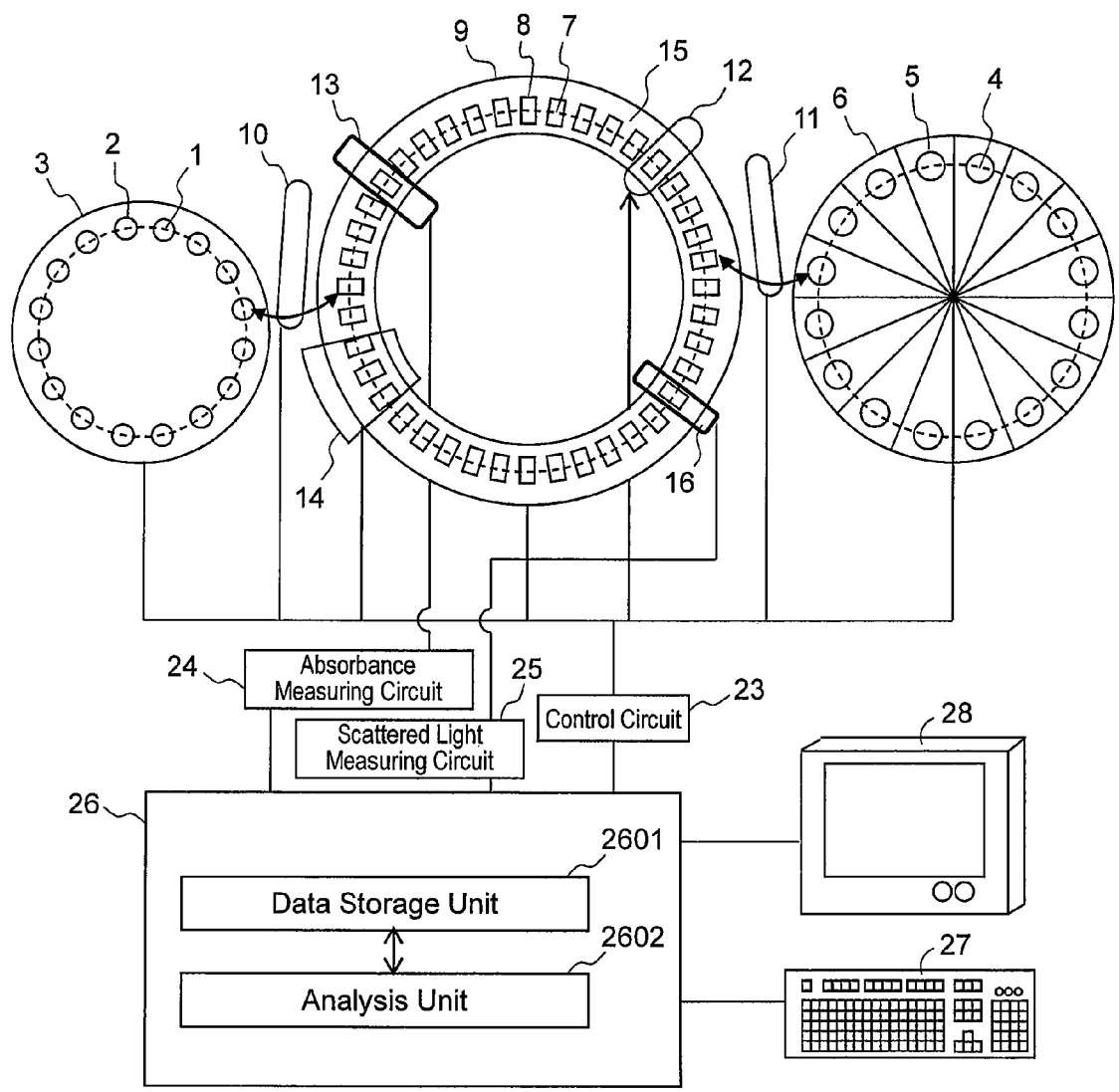
FIG. 5 shows an example of the entire configuration of an automatic analysis device (Embodiment 2).

FIG. 5 shows an example of the entire configuration of an automatic analysis device in accordance with this embodiment. Portions that are common to FIG. 5 and FIG. 1 are denoted by common reference numerals.

The automatic analysis device in accordance with this embodiment includes three types of discs, which include a sample disc 3, a reagent disc 6, and a reaction disc 9, a dispensing mechanism for moving samples and reagents to/from such discs, a control circuit 23 therefor, an absorbance measuring circuit 24 that measures the absorbance of a reaction solution, a scattered light measuring circuit 25 that measures scattered light from a reaction solution, a data processing unit 26 that processes data measured with each measuring circuit, and an input unit 27 and an output unit 28 that are interfaces with the data processing unit 26.

It should be noted that the data processing unit 26 includes a data storage unit 2601 and an analysis unit 2602. The first data processing unit 261 and the second data processing unit 262 in Embodiment 1 partially constitute the functions of the analysis unit 2602. The data storage unit 2601 stores control data, measured data, data used for analyzing data, analysis result data, and the like. The input unit 27 and the output unit 28 receive and output data from/to the data storage unit 2601. The example in FIG. 5 represents a case where the input unit 27 is a keyboard, but other input devices, such as a touch panel and a numeric keypad, may also be used.

A plurality of sample cups 2, which are storage containers for a sample 1, are arranged on the circumference of the sample disc 3. The sample 1 is blood, for example. A plurality of reagent bottles 5, which are storage containers for a reagent 4, are arranged on the circumference of the reagent disc 6. A plurality of cells 8, each of which is a storage container for a reaction solution 7 obtained by mixing the sample 1 with the reagent 4, are arranged on the circumference of the reaction disc 9.

A sample dispensing mechanism 10 is a mechanism used to move the sample 1 from the sample cup 2 to the cell 8 by a given amount. The sample dispensing mechanism 10 includes, for example, a nozzle that discharges or sucks a solution, a robot that positions the nozzle at a predetermined location and transports it, and a pump that discharges a solution from the nozzle or causes a solution to be sucked into the nozzle. A reagent dispensing mechanism 11 is a mechanism used to move the reagent 4 from the reagent bottle 5 to the cell 8 by a given amount. The reagent dispensing mechanism 11 also includes, for example, a nozzle that discharges or sucks a solution, a robot that positions the nozzle at a predetermined location and transports it, a pump that discharges a solution from the nozzle or causes a solution to be sucked into the nozzle.

An agitation unit 12 is a functional unit that agitates and mixes the sample 1 with the reagent 4 in the cell 8. A washing unit 14 is a functional unit that discharges the reaction solution 7 from the cell 8 in which an analysis process has terminated and thereafter washes the cell 8. A next sample 1 is dispensed again from the sample dispensing mechanism 10 into the cell 8 that has been washed, while a new reagent 4 is dispensed from the reagent dispensing mechanism 11 into the cell 8 so as to be used for another reaction process.

The cells 8 on the reaction disc 9 are immersed in a constant-temperature fluid 15 in a thermostatic bath with controlled temperature and flow rate. Therefore, the cells 8 and the reaction solution 7 therein are kept at a constant temperature even while they are moved on the reaction disc 9. In this embodiment, water is used as the constant-temperature fluid 15, and the temperature of the water is adjusted in the range of 37±0.1° C. by the control circuit 23. Needless to say, a medium that is used as the constant-temperature fluid 15 and the temperature herein are only exemplary.

An absorbance measuring unit 13 and a scattered light measuring unit 16 are arranged on a part of the circumference of the reaction disc 9.

Figure 6:
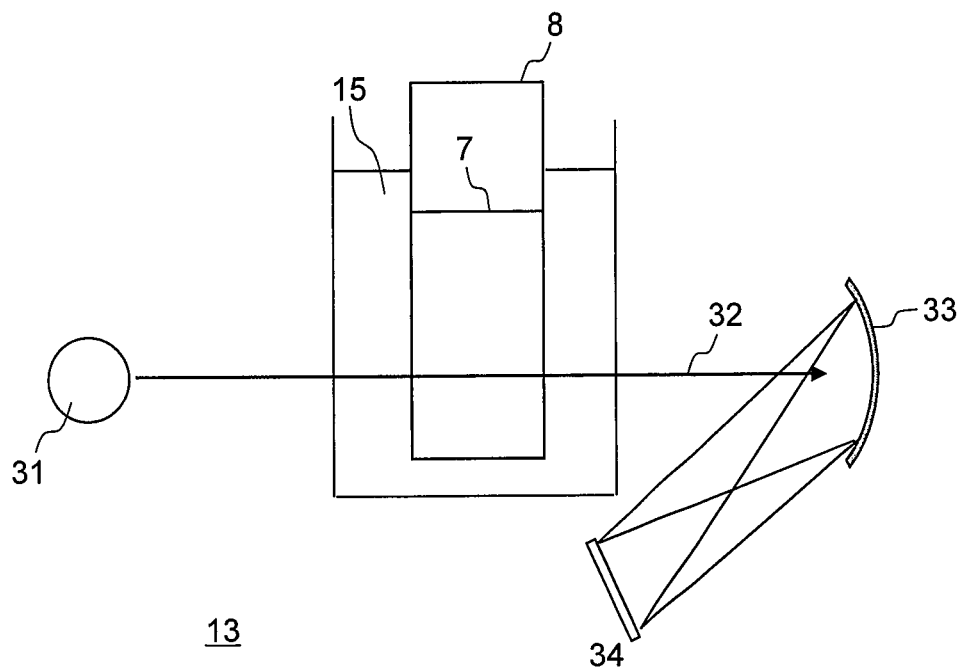
FIG. 6 shows an exemplary schematic configuration of an absorbance measuring unit.

FIG. 6 shows an exemplary configuration of the absorbance measuring unit 13. The absorbance measuring unit 13 shown in FIG. 6 has a structure in which the cell 8 is irradiated with light emitted from a halogen lamp light source 31, and light 32 that has passed through the cell 8 is split by a diffraction grating 33, and the split light is received by a photodiode array 34. The wavelengths of light that are received by the photodiode array 34 include 340 nm, 405 nm, 450 nm, 480 nm, 505 nm, 546 nm, 570 nm, 600 nm, 660 nm, 700 nm, 750 nm, and 800 nm. Light-reception signals received by such light receivers are transmitted to the data storage unit 2601 in the data processing unit 26 via the absorbance measuring unit 13. Herein, the absorbance measuring unit 13 acquires a light-reception signal in each wavelength range at regular intervals, and outputs the value of the amount of the acquired light to the data processing unit 26.

Figure 7:
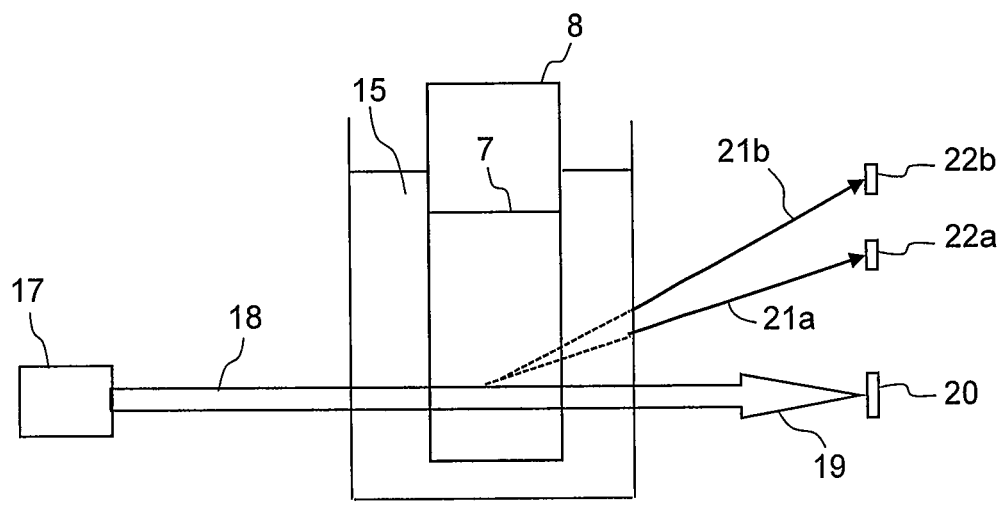
FIG. 7 shows an exemplary schematic configuration of a scattered light measuring unit.

FIG. 7 shows an exemplary configuration of the scattered light measuring unit 16. In this embodiment, a LED light source unit, for example, is used for the light source 17. Irradiation light 18 emitted from the LED light source unit irradiates the cell 8 located on the optical path, and transmitted light 19 that has passed through the cell 8 is received by a transmitted light receiver 20. For the wavelength of the irradiation light, 700 nm is used, for example. Although a LED light source unit is used as the light source 17 in this embodiment, it is also possible to use a laser source, a xenon lamp, a halogen lamp, or the like.

The scattered light measuring unit 16 receives scattered light 21a in a direction, which is away from the optical axis of the irradiation light 18 or the transmitted light 19 by an angle of 20° in the air, with a scattered light receiver 22a. In addition, the scattered light measuring unit 16 receives scattered light 21b in a direction, which is away from the optical axis of the irradiation light 18 or the transmitted light 19 by an angle of 30° in the air, with a scattered light receiver 22b. For the scattered light receivers 22a and 22b, photodiodes are used, for example. The signals received by the scattered light receivers 22a and 22b are transmitted to the data storage unit 2601 in the data processing unit 26 via the scattered light measuring unit 16. The scattered light measuring unit 16 also acquires the two signals received at different light-receiving angles at regular intervals, and outputs the value of the amount of the acquired light to the data processing unit 26.

The scattered light receivers 22a and 22b are arranged on a plane that is generally perpendicular to the direction in which the cell 8 is moved by the rotation of the reaction disc 9. Herein, the reference position of the light-receiving angle (i.e., the starting point of scattering) is set at the center of the optical path of light that passes through the cell 8.

Although FIG. 7 illustrates a case where the scattered light receivers 22a and 22b are arranged so as to correspond to the light-receiving angles of 20° and 30°, respectively, it is also possible to provide a configuration in which a single linear array that holds a number of receivers therein is arranged so that scattered light with a plurality of angles are received at once. When the linear array is used, the selection range of the light-receiving angles can be increased. It is also possible to arrange not a light receiver but optics such as fibers or lenses so that light is guided to scattered light receivers arranged at different locations.

[Measurement of the Concentration of a Substance to be Measured and Determination of if the Measurement Result is Normal/Abnormal]

Quantitative determination of the concentration of a substance to be measured, which is contained in the sample 1, is performed in accordance with the following procedures. First, the control circuit 23 washes the cell 8 using the washing unit 14. Then, the control circuit 23 dispenses a given amount of sample 1 in the sample cup 2 into the cell 8 using the sample dispending mechanism 10. Next, the control circuit 23 dispenses a given amount of reagent 4 in the reagent bottle 5 into the cell 8 using the reagent dispensing mechanism 11.

In dispensing each solution, the control circuit 23 rotationally drives the sample disc 3, the reagent disc 6, or the reaction disc 9 using the corresponding driving unit. At this time, each of the sample cup 2, the reagent bottle 5, and the cell 8 is positioned at a predetermined dispensing location in accordance with the drive timing of the corresponding dispensing mechanism.

Next, the control unit 23 controls the agitation unit 12 to agitate the sample 1 and the reagent 4 dispensed in the cell 8, thereby producing a reaction solution 7. When the reaction disc 9 is rotated, the cell 8, which stores the reaction solution 7, passes through each of the measurement position where the absorbance measuring unit 13 is arranged and the measurement position where the scattered light measuring unit 16 is arranged. Each time the cell 8 passes through the measurement position, transmitted light or scattered light from the reaction solution 7 is measured via the corresponding absorbance measuring unit 13 or scattered light measuring unit 16. In this embodiment, the measurement time of each unit is about 10 minutes. Measured data obtained with the absorbance measuring unit 13 and the scattered light measuring unit 16 are sequentially output to the data storage unit 2601, and are accumulated as reaction process data.

While the reaction process data is accumulated, another reagent 4 is additionally dispensed into the cell 8 by the reagent dispensing mechanism 11 if necessary, and is agitated by the agitation unit 12 so that measurement for further another given time is performed. Accordingly, reaction process data acquired at regular time intervals are stored in the data storage unit 1601.

Figure 8:
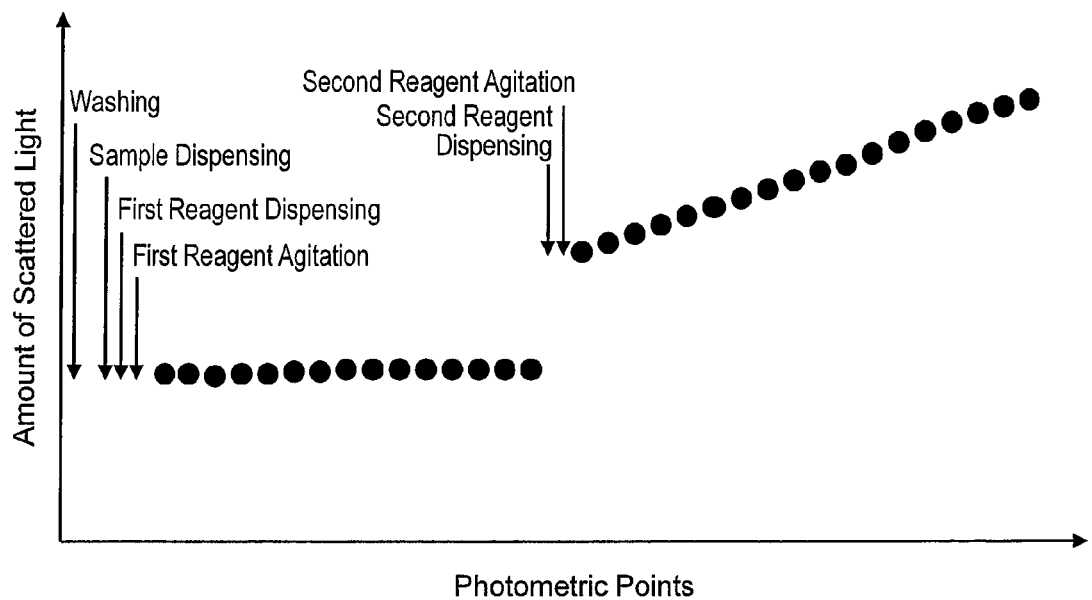
FIG. 8 shows an example of reaction process data.

FIG. 8 shows an example of the reaction process data. Photometric points shown on the abscissa axis of FIG. 8 represent the order in which reaction process data are measured. Meanwhile, the ordinate axis of FIG. 8 represents the amount of scattered light measured by the scattered light measuring circuit 25. Although FIG. 8 represents reaction process data corresponding to a given light-receiving angle, the scattered light measuring circuit 25 in accordance with this embodiment separately outputs reaction process data corresponding to a light-receiving angle of 20° and reaction process data corresponding to a light-receiving angle of 30°.

The analysis unit 2602 calculates a change in the amount of light that occurred in a given period of time, which has been specified via an analysis setting screen (not shown), as a computed value. Herein, the given period of time used to calculate the computed value is defined by specifying the computation start point and the computation end point from among the photometric points. It should be noted that the computed value is computed as a difference between the amount of light at the computation start point and that at the computation end point.

The data storage unit 2601 stores in advance calibration curve data that represents the relationship between the computed value and the concentration of the substance to be measured. The analysis unit 2602 matches the computed value against the calibration curve data to quantitatively determine the concentration of the substance to be measured. The value of the quantitatively determined concentration is displayed via the output unit 28.

The analysis unit 2602 calculates a value, which is obtained from dividing a computed value corresponding to a light-receiving angle of 30° by a computed value corresponding to a light-receiving angle of 20°, as the intensity ratio of scattered light. If the intensity ratio of scattered light satisfies a predetermined condition, the analysis unit 2602 determines that the result of the quantitative determination represents a normally measured value.

Meanwhile, if the calculated intensity ratio of scattered light does not satisfy a predetermined condition, the analysis unit 2602 determines that the result of the quantitative determination represents abnormal measurement including influence of foreign-body reactions. The result of determination is also stored in the data storage unit 2601.

It should be noted that data that is necessary to control each unit or perform analysis is input to the data storage unit 2601 from the input unit 27. A variety of pieces of data stored in the data storage unit 2601, measurement results, analysis results, alarm, and the like are displayed by the output unit 28.

[Analysis Setting Screen]

Figure 9:
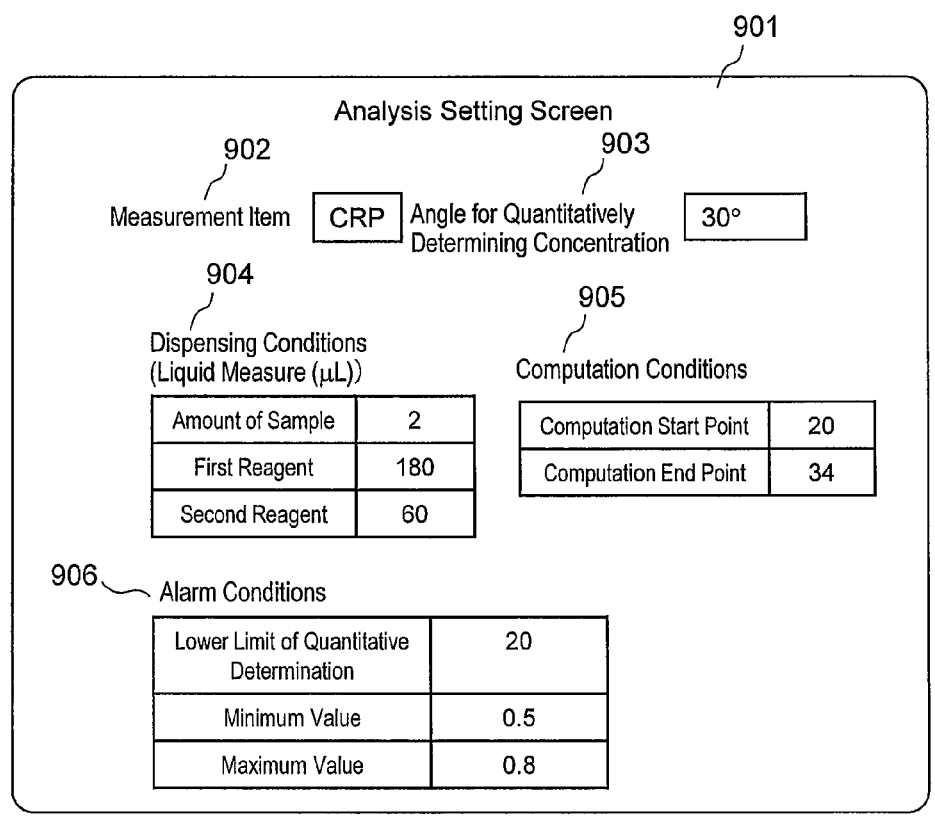
FIG. 9 shows an example of an analysis setting screen.

FIG. 9 shows an example of an analysis setting screen. A user uses an analysis setting screen 901, and sets an angle 903 for quantitatively determining the concentration, dispensing conditions 904, computation conditions 905, and alarm conditions 906 for each measurement item 902. FIG. 9 represents a case where the measurement item 902 is CRP (C-reactive protein) and the angle 903 for quantitatively determining the concentration is 30°. In addition, FIG. 9 represents a case where the amount of sample is set to 2 µL, the first reagent is set to 180 µL, and the second reagent is set to 60 µL as the dispensing conditions 904.

Further, FIG. 9 represents a case where the computation start point is set to the 20th measurement point and the computation end point is set to the 34th measurement point as the computation conditions 905. Thus, in the case of FIG. 9, the analysis unit 2602 calculates a computed value from a change in the amount of light measured along with a reaction that occurred in a given period of time from the 20th measurement point to the 34th measurement point.

Furthermore, FIG. 9 represents an example in which the lower limit of quantitative determination of the computed value is set to "20," the minimum value of the intensity ratio of scattered light is set to "0.5," and the maximum value of the intensity ratio of scattered light is set to "0.8" as the alarm conditions 906. Thus, in the case of FIG. 9, when the computed value is "15," for example, the analysis unit 2602 determines that the value is not in the normal range.

The lower limit of quantitative determination of the computed value is set as the alarm condition 906 for the following reason. In the measurement circumstances in which computed values are less than or equal to the lower limit of quantitative determination, measured values are likely to vary, because the calculated intensity ratio of scattered light (i.e., the ratio of the computed values) will also vary. Thus, determination of whether or not to output an alarm is performed only when a computed value that is above the lower limit of quantitative determination is calculated. Although the maximum value that provides the upper limit of the range in which the intensity ratio of scattered light is normal is set to "0.8" in FIG. 9, the maximum value may also be "0.9."

The numerical values that provide the normal range of the alarm conditions 906 may be manually input by a user with reference to a parameter that is recommended by the reagent manufacturer for each reagent. Alternatively, the automatic analysis device may be provided with a function of automatically setting alarm conditions so that values and the like that are recommended by the reagent manufacturer are automatically set in advance for each reagent.

It should be noted that a user specifies a correspondence between the sample number of blood to be measured and the sample position on the sample disc and also specifies test items via a separate screen (not shown).

[Processing Operations of Automatic Analysis Device]

Figure 10:
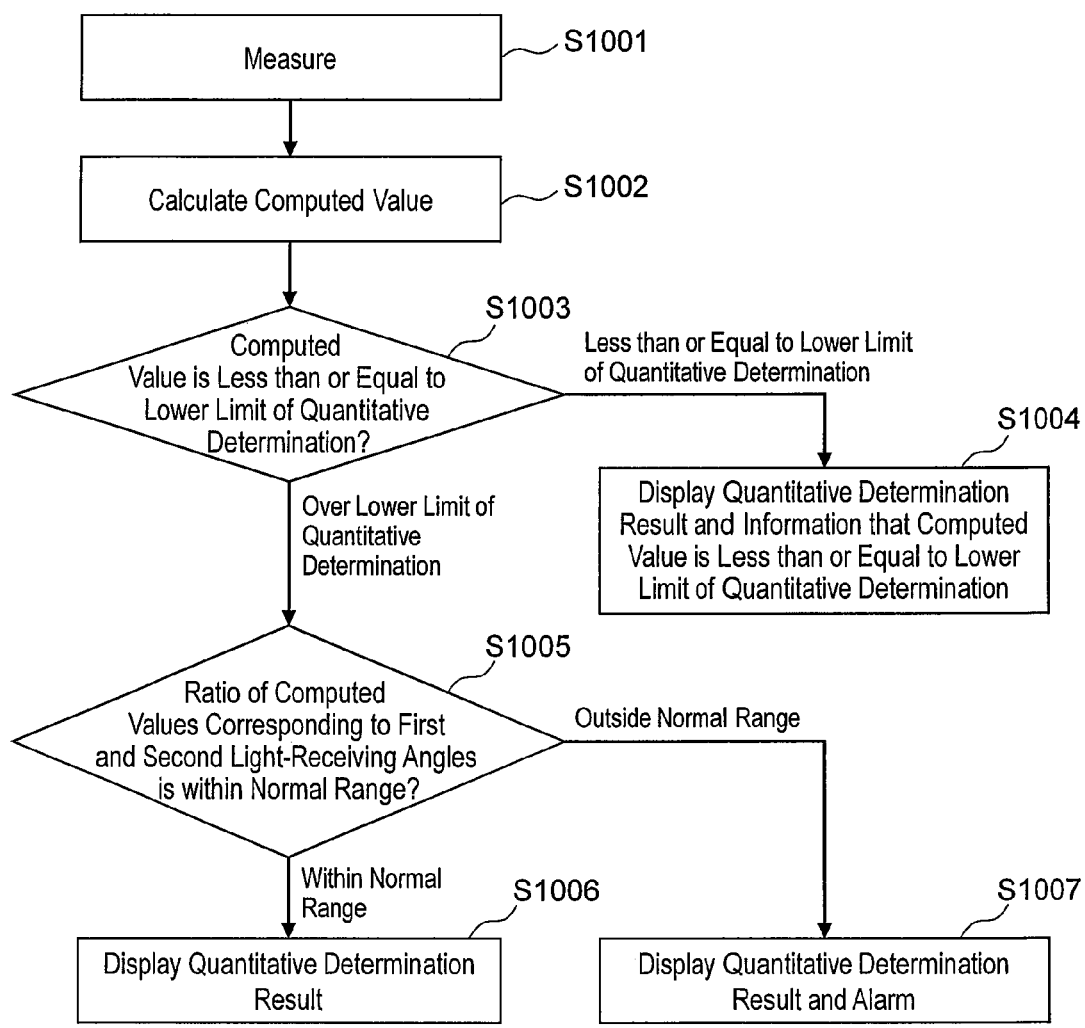
FIG. 10 is a flowchart showing the processing procedures from when measurement is started till when measurement results are displayed.

FIG. 10 shows an example of processing operations executed with the automatic analysis device in accordance with this embodiment. FIG. 10 represents a series of processing operations from when measurement of concentration by the automatic analysis device is started till when the result of quantitative determination is displayed.

As the preprocessing, the control circuit 23 determines if the analysis conditions and test items have been set. Upon checking the setting of the analysis conditions and test items, the control circuit 23 controls each unit of the automatic analysis device, and starts measurement of the concentration of a predetermined sample specified by a user (step S1001). Along with the start of measurement, the intensity of scattered light is measured for each light-receiving angle, and the measured intensity of scattered light is stored as time-series data (i.e., reaction process data) in the data storage unit 2601.

Next, the analysis unit 2602 reads predetermined measurement points from the reaction process data to compute a difference in the amount of light, and outputs the difference as the computed value (step S1002). Such computed value is also stored in the data storage unit 2601. In addition, the analysis unit 2602 matches the computed value against the calibration curve data to quantitatively determine the concentration of the substance to be measured.

After that, the analysis unit 2602 determines if the computed value is less than or equal to the lower limit of quantitative determination (step S1003). If the computed value is less than or equal to the lower limit of quantitative determination, the analysis unit 2602 displays on a screen the result of quantitative determination as well as information to the effect that the computed value is less than or equal to the lower limit of quantitative determination via the output unit 28 (step S1004).

Meanwhile, if the computed value is over the lower limit of quantitative determination, the analysis unit 2602 computes the computed value ratio (i.e., the intensity ratio of scattered light) between the computed value corresponding to the first light-receiving angle (e.g., 20°) and the computed value corresponding to the second light-receiving angle (e.g., 30°), and determines if the computed value ratio (i.e., the intensity ratio of scattered light) is within a normal range (step S1005). In this embodiment, the computed value ratio (i.e., the intensity ratio of scattered light) is calculated by dividing the computed value corresponding to the light-receiving angle of 30° by the computed value corresponding to the light-receiving angle of 20°.

If the computed value ratio (i.e., the intensity ratio of scattered light) is within the normal range, the analysis unit 2602 displays on the screen the result of quantitative determination via the output unit 28. It is also possible to display on the screen information to the effect that the result of quantitative determination does not include influence of foreign-body reactions and the computed value ratio (i.e., the intensity ratio of scattered light) at the same time.

In contrast, if the computed value ratio (i.e., the intensity ratio of scattered light) is outside the normal range, the analysis unit 2602 displays the result of quantitative determination as well as an alarm to the effect that the result of quantitative determination includes influence of foreign-body reactions.

[Result Display Screen]

Figure 11:
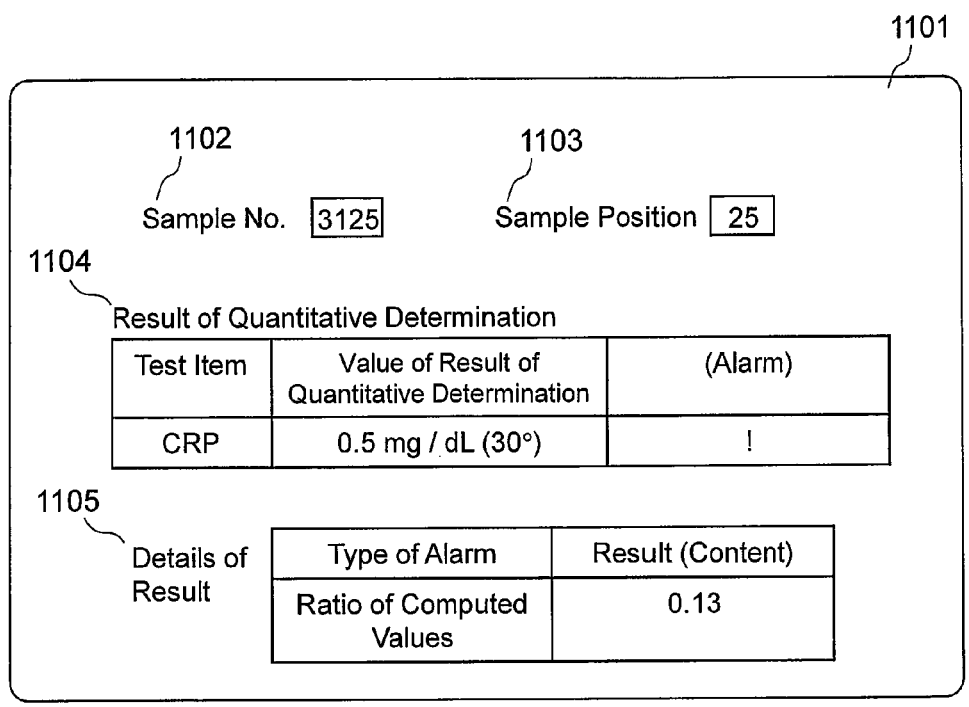
FIG. 11 shows an exemplary display screen of measurement results.

FIG. 11 shows an example of a result display screen. A result display screen 1101 includes a sample No. 1102, a sample position 1103, a result of quantitative determination 1104, and details of result 1105. In FIG. 11, the sample No. 1102 is "3125," and the sample position 1103 that provides the position on the sample disc is "25."

It should be noted that the result of quantitative determination 1104 includes test items, the value of the result of quantitative determination, and an alarm as the display items. This embodiment shows that the test item is "CRP" and the value of the result of quantitative determination is "0.5 mg/dL." Further, a light-receiving angle of 30°, which has been used to measure concentration, is also shown. As the result of quantitative determination herein is an abnormal measurement including influence of foreign-body reactions, "!" is displayed on the alarm report field. An alarm is displayed not only when the computed value is less than or equal to the lower limit of quantitative determination, but also when the intensity ratio of scattered light is outside the normal range. Needless to say, different symbols or marks may also be used for displaying an alarm.

The alarm report field may also be indicated by a specific word or phrase, such as "less than or equal to the lower limit of quantitative determination," "abnormal angle ratio," or "influence of foreign-body reactions present." When such a display pattern is used, information on the alarm can be displayed clearly and quantitatively. Consequently, a user is able to specifically understand why an alarm is displayed. It should be noted that when the value of the result of quantitative determination indicates a normal measurement, the alarm report field may be blank or be indicated by a specific term, such as "normal."

As the details of result 1105, the type of an alarm and the results (information) thereof are shown as the display items. FIG. 11 represents that the type of an alarm is based on the "computed value ratio." Specifically, FIG. 11 represents that the computed value is "0.13." Needless to say, when the cause of an alarm is "less than or equal to the lower limit of quantitative determination," the phrase "less than or equal to the lower limit of quantitative determination" as well as the computed value calculated at that time is displayed.

[Description of Normal Range]

Figure 12:
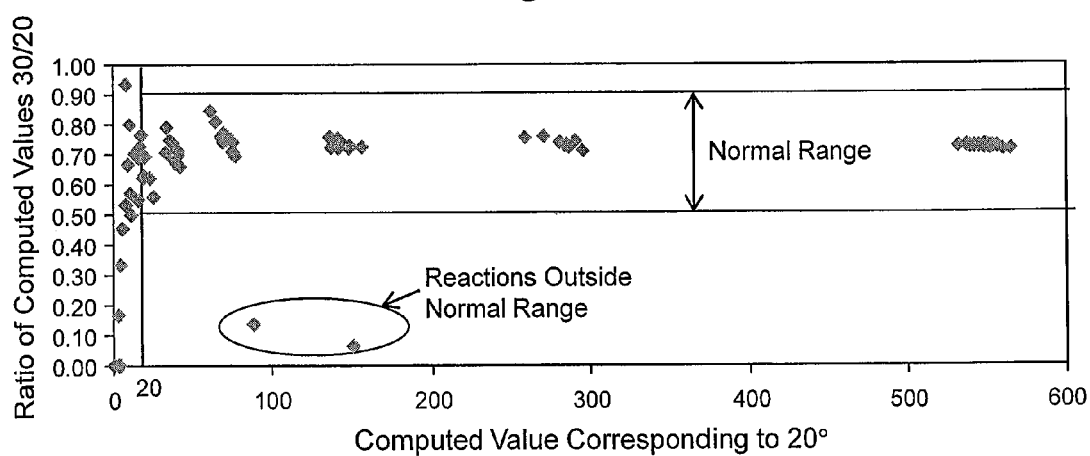
FIG. 12 shows the relationship between a computed value corresponding to scattered light intensity at a light-receiving angle of 20° and a ratio of a computed value corresponding to scattered light intensity at a light-receiving angle of 20° and a computed value corresponding to scattered light intensity at a light-receiving angle of 30° (30°/20°).

Finally, with respect to the specific measurement results, the relationship between reactions in the normal range and reactions outside the normal range is shown. FIG. 12 represents, regarding a total of 60 reactions that differ in the concentrations of CRP contained in samples within a given range, the relationship between the computed value corresponding to 20° and the computed value ratio (i.e., the intensity ratio of scattered light) of 30°/20°. In FIG. 12, the abscissa axis represents the computed value corresponding to the light-receiving angle of 20°, and the ordinate axis corresponds to the intensity ratio of scattered light. It should be noted that marks in the graph represent individual reactions.

In the case of FIG. 12, the lower limit of quantitative determination is fixed at "20" of the computed value corresponding to 20°. Thus, a reaction whose computed value is less than or equal to "20" (in FIG. 12, reactions that are mapped on the left side of the computed value of "20" are the targets to be displayed as alarms as the values are less than or equal to the lower limit of quantitative determination. Meanwhile, even when the computed value is above "20," the range in which the computed value ratio (i.e., the intensity ratio of scattered light) is regarded as normal is in the range of 0.5 to 0.9 that are sandwiched by two threshold lines. Thus, the example in FIG. 12 represents that there are two reactions whose computed value ratio (i.e., the intensity ratio of scattered light) are outside the normal range.

With the automatic analysis device in accordance with the above embodiment, it is possible to inform a user about if the result of quantitative determination conducted with the scattered light measurement method is highly reliable as the measured value. Accordingly, it is possible to further improve the reliability by, for example, executing measurement again for samples from which results of quantitative determination with low reliability were obtained.

Further, according to this embodiment, it is possible to check the type of a cause why an alarm is output, the measurement results at that time, and the like on the screen by displaying the information on the screen. With such a function mounted, a user is able to check the cause why the alarm is output.

[Other Embodiments]

The present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute a structure of another embodiment.

Some or all of the aforementioned structures, functions, processing units, processing means, and the like may be implemented as an integrated circuit or other hardware, for example. Alternatively, each of the aforementioned structures, functions, and the like may be implemented such that a processor analyzes and executes a program that implements each function. That is, each of the aforementioned structures, functions, and the like may be implemented as software. Information such as the program that implements each function, tables, and files can be stored in a storage device such as memory, a hard disk, or a SSD (Solid State Drive); or a storage medium such as an IC card, an SD card, or a DVD.

In addition, the control lines and information lines represent those that are considered to be necessary for the description, and do not necessarily represent all control lines and information lines that are necessary for a product. Thus, in practice, almost all structures may be considered to be mutually connected.

REFERENCE SIGNS LIST

1 Sample
2 Sample cup
3 Sample disc
4 Reagent
5 Reagent bottle
6 Reagent disc
7 Reaction solution
8 Cell
9 Reaction disc
10 Sample dispensing mechanism
11 Reagent dispensing mechanism
12 Agitation unit
13 Absorbance measuring unit
14 Washing unit
15 Constant-temperature fluid
16 Scattered light measuring unit
160 Light source
161 Light receiver
162 Light receiver
17 Light source
18 Irradiation light
19 Transmitted light
20 Transmitted light receiver
21a,21b Scattered light
22a,22b Scattered light receiver
23 Control circuit
24 Absorbance measuring circuit
25 Scattered light measuring circuit
26 Data processing unit
261 First data processing unit
262 Second data processing unit
2601 Data storage unit
2602 Analysis unit
27 Input unit
28 Output unit

The invention claimed is:

1. An automatic analysis device comprising:
a reaction disk holding a plurality of cells, one or more of the cells holding a reaction solution;
a light source configured to irradiate a respective reaction solution held by a cell of the plurality of cells with light;
a plurality of light receivers, including a first light receiver and a second light receiver, each configured to receive scattered light generated from the reaction solution at different light-receiving angles, the first light receiver receiving light at a first angle and the second light receiver receiving light a second angle, wherein the plurality of light-receiving angles are each less than or equal to 35° with respect to an optical axis of the light irradiated by the light source;
a display unit; and
a computer connected to the reaction disk, light source, each of the plurality of light receivers, and the display unit, the computer programmed to:
receive data from each of the plurality of light receivers as reaction process data,
quantitatively determine a concentration of a substance in the reaction solution based on reaction process data of the first light receiver,
calculate a ratio of a computed value of the reaction process data of the first light receiver received at the first angle and a computed value of the reaction process data of the second light receiver received at the second angle,
determine if the quantitative determination of the concentration of the substance has been performed normally based on whether the calculated ratio is less than a predetermined threshold, and display an alarm, on a screen of the display unit, if the concentration of the substance has not been performed normally.

2. The automatic analysis device according to claim 1, wherein the computer is programmed to display a type of the alarm and a computed value or a ratio of a plurality of computed values calculated at that time on the screen that corresponds to the alarm, the type of the alarm indicating a cause of output of the alarm.

3. The automatic analysis device according to claim 1, wherein the computer is programmed to display on the display unit a setting screen for receiving, as alarm conditions settings that include a minimum value and a maximum value, the minimum value and the maximum value providing a normal range of a ratio of computed values corresponding to a plurality of pieces of reaction process data measured by the respective light receivers, and receive inputs of the minimum value and the maximum value providing a normal range, determine if the quantitative determination of the concentration of the substance has been performed normally based on whether the concentration is within the normal range provided by the minimum value and the maximum value.

4. The automatic analysis device according to claim 1, wherein the plurality of light receivers are disposed in a linear array.

5. The automatic analysis device according to claim 1, wherein the computer is programmed to: display a type of the alarm and a computed value or a ratio of a plurality of computed values calculated at that time on the screen that corresponds to the alarm, the type of the alarm indicating a cause of output of the alarm, display on the display unit a setting screen for receiving, as alarm conditions settings that include a minimum value and a maximum value, the minimum value and the maximum value providing a normal range of a ratio of computed values corresponding to a plurality of pieces of reaction process data measured by the respective light receivers, and receive inputs of the minimum value and the maximum value providing a normal range, determine if the quantitative determination of the concentration of the substance has been performed normally based on whether the concentration is within the normal range provided by the minimum value and the maximum value, and wherein the plurality of light receivers are disposed in a linear array.

\* \* \* \* \*